United States Patent [19]

Leeson

[11] Patent Number: 4,765,985
[45] Date of Patent: Aug. 23, 1988

[54] DEVICES AND METHODS FOR TREATING MEMORY IMPAIRMENT

[75] Inventor: Lewis J. Leeson, Roseland, N.J.

[73] Assignee: Ciba-Geigy Corporation, Ardsley, N.Y.

[21] Appl. No.: 51,781

[22] Filed: May 20, 1987

Related U.S. Application Data

[62] Division of Ser. No. 708,466, Mar. 5, 1985, Pat. No. 4,680,172.

[51] Int. Cl.[4] .......................... A61F 13/02; A61K 9/70
[52] U.S. Cl. ..................... 424/449; 514/359; 514/411; 514/422
[58] Field of Search ................ 424/449, 448; 514/359, 514/411, 422

[56] References Cited

U.S. PATENT DOCUMENTS

| | | | |
|---|---|---|---|
| 3,742,951 | 7/1973 | Zaffaroni | 128/268 |
| 3,760,805 | 9/1973 | Higuchi | 128/260 |
| 3,760,806 | 9/1973 | Leeper et al. | 128/260 |
| 3,764,984 | 10/1973 | McCarthy | 340/168 |
| 3,797,494 | 3/1974 | Zaffaroni | 128/268 |
| 3,845,770 | 11/1974 | Theeuwes et al. | 128/260 |
| 3,916,899 | 11/1975 | Theeuwes | 128/260 |
| 3,921,636 | 11/1975 | Zaffaroni | 128/260 |
| 3,987,790 | 10/1976 | Eckenhoff et al. | 128/260 |
| 3,996,934 | 12/1976 | Zaffaroni | 128/268 |
| 4,031,894 | 6/1977 | Urquhart et al. | 128/268 |
| 4,137,300 | 1/1979 | Sheth | 424/21 |
| 4,144,317 | 3/1979 | Higuchi | 424/14 |
| 4,278,667 | 7/1981 | Madison et al. | 424/232 |
| 4,597,961 | 7/1986 | Etscorn | 424/28 |

FOREIGN PATENT DOCUMENTS

| | | |
|---|---|---|
| 40861 | of 1981 | European Pat. Off. . |
| 89548 | 9/1983 | European Pat. Off. . |
| 108218 | 5/1984 | European Pat. Off. . |
| 116238 | 8/1984 | European Pat. Off. . |
| 178140 | 4/1986 | European Pat. Off. . |
| 3528979 | 2/1986 | Fed. Rep. of Germany . |
| 2142822 | 1/1985 | United Kingdom . |
| 2163347 | 7/1986 | United Kingdom . |

OTHER PUBLICATIONS

Neurobiology of Aging, vol. 4(2), pp. 139–145 (1983).
New England J. of Med., p. 946, (8/27/82).
Southern Medical Journal, vol. 55, pp. 1134–1138 (11/62).
J. Pharma. Pharmacol., vol. 31, pp. 140–147 (1979).
Arch. Neurol, vol. 36: 501–503 (8/79).
Brit. J. Psychiat. 138: 46–50 (1981).
"Drug Naloxone Finds Two New Uses", C&E News, (3/28/83).
Science 201: 271–274 (7/21/78).
Annual Reports in Med. Chem., vol. 53, p. 16.
Emr, Process Report on Senile Dementia of the Alzheimers Type (2/81).

Primary Examiner—Delbert R. Phillips
Assistant Examiner—Nathan M. Nutter
Attorney, Agent, or Firm—Irving M. Fishman

[57] ABSTRACT

A device for the transdermal administration of a drug for the treatment of memory impairment comprising:
(a) a drug impermeable backing layer;
(b) a drug permeable rate controlling membrane sealed to one side of said backing layer as to define at least one drug reservoir compartment therebetween;
(c) an adhesive layer;
(d) a drug or composition thereof within said hollow drug reservoir; said drug comprising a memory improving effective amount of a compound having the formula

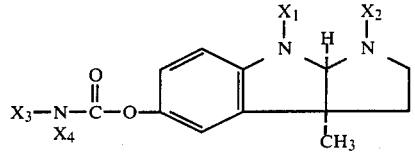

wherein $X_1$, $X_2$, $X_3$, $X_4$, independently represent —H or lower alkyl;
said composition comprising said drug and at least one pharmaceutically acceptable adjunct; whereby said drug is delivered in a controlled, continuous manner to a patient to which said device has been applied.

11 Claims, No Drawings

DEVICES AND METHODS FOR TREATING MEMORY IMPAIRMENT

This is a divisional of application Ser. No. 708,466, filed on Mar. 5, 1985, and now U.S. Pat. No. 4,680,172.

The present invention is directed to devices and methods for treating memory impairment. More particularly, the present invention is directed to providing devices for the controlled release of compounds effective in treating memory impairment, and to methods for treating memory impairment comprising such controlled release Senile dementia of the Alzheimer's type (SDAT), a pervasive and devastating affliction mainly affecting the elderly, is an example of memory impairment, the treatment of which is the goal of the present invention.

Acetylcholine is believed to be involved in learning and memory mechanisms; see Sitaram et al, Science, 201, 274 (1978), and Davis et al, Science, 201, 272 (1978). The Sitaram et al and Davis et al articles suggest that arecoline, a cholinergic agonist, and physostigmine, an acetylcholinesterase inhibitor, respectively, may be effective in treating memory impairment. Christie et al, however, have suggested that neither arecoline nor physostigmine offers a practical therapy for SDAT; see the British Journal of Psychiatry, 138, 46 at 49 (1981). This may, at least in part, be due to the short-lived effects of these compounds as suggested in the "Progess Report on Senile Dementia of the Alzheimer's Type" dated February 19, 1981 prepared by Marian Emr of the National Institute on Aging at page 20.

Naloxone is also believed to be effective in treating memory loss; see Chemical and Engineering News, 32 (Mar. 28, 1983). The use of Naloxone for treating SDAT is, however, still under investigation; see FDC Reports of Mar. 21, 1983.

There is, therefore, a need for developing devices and methods for treating memory impairment, especially SDAT, practically and effectively.

OBJECTS OF THE INVENTION

Accordingly, the objects of the present invention are:
devices and methods effective in treating memory impairment
devices and methods which provide for the controlled release of compounds effective in treating memory impairment; and
devices and methods for treating memory impairment by means of the controlled release of arecoline and derivatives, physostigmine and derivatives, naloxone and derivatives, and nicotine and derivatives.

SUMMARY OF THE INVENTION

The above and other objectives as will become apparent from the following description have been achieved by providing a device for treating memory impairment comprising an effective amount of compound selected from formula I:

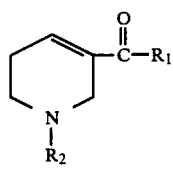
(I)

werein $R_1$ represents OH, lower alkoxy, or $NR_3R_4$ and $R_2$, $R_3$ and $R_4$ independently represent H or lower alkyl;

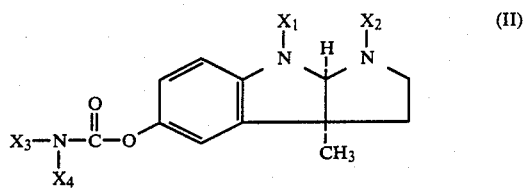
(II)

wherein $X_1$, $X_2$, $X_3$, $X_4$, independently represent H or lower alkyl;

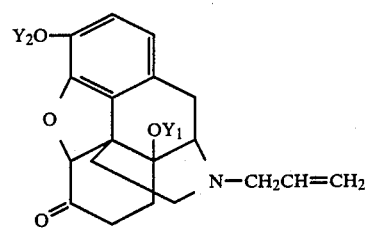
(III)

wherein $Y_1$ and $Y_2$ independently represent H, lower alkyl or lower alkycarbonyl; and

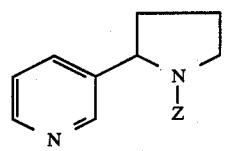
(IV)

wherein Z represents H or lower alkyl; and a means for delivering the compound at a continuous, controlled rate and to methods for treating memory impairment using such devices.

DETAILED DESCRIPTION OF THE INVENTION

The effective compounds of the present invention include arecoline, physostigmine, naloxone, and nicotine. Some derivatives are also included in the invention.

Arecoline and arecoloine derivatives have formula I as follows:

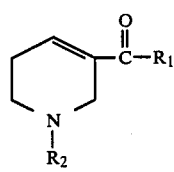
(I)

In formula I, $R_1$ represents OH, lower alkoxy, or $NR_3R_4$ and $R_2$, $R_3$ and $R_4$ independently represent H or loewr alkyl.

Physostigmine and physostigmine derivatives may be represented by formula II as follows:

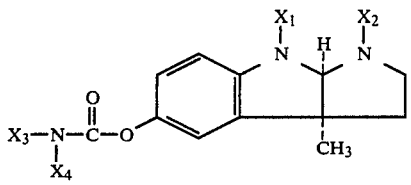

(II)

In formula II, $X_1$, $X_2$, $X_3$, and $X_4$ independently represent H or lower alkyl.

Naloxone and naloxole derivatives may be represented by formula III as follows:

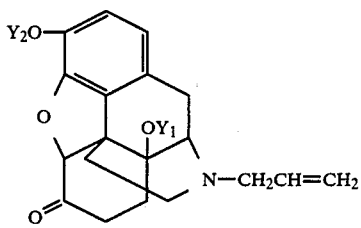

(III)

In formula III, $Y_1$ and $Y_2$ independently represent H, lower alkyl, or lower alkylcarbonyl (acyl).

Nicotine and derivatives may be represented by formula IV:

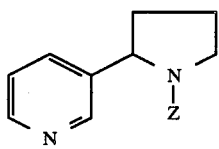

(IV)

In formula IV, Z represents H or lower alkyl.

In the compounds of the present invention, the term "lower alkyl" and "lower alkoxy" refer to alkyl and alkoxy groups having up to and including 7 carbon atoms and preferably up to and including 4 carbon atoms. Some examples of alkyl groups include methyl, ethyl, propyl, isopropyl, n-butyl, isobutyl, secondary butyl, tertiary butyl, pentyl, isopentyl, neopentyl, hexyl, isohexyl, and heptyl. Some examples of alkoxy groups include the oxides corresponding to the above alkyl groups.

Accordingly, the preferred compounds having formula I are those $R_1$ and $R_2$ independently represent H or lower alkyl or alkoxy having up to 4 carbon atoms such as methyl, ethyl, and isopropyl. The compounds having formula II are preferably those wherein $X_1$, $X_2$, $X_3$, and $X_4$ represent H or lower alkyl having up to 4 carbon atoms such as methyl, ethyl and isopropyl. The compounds having formula III are preferably those wherein $Y_1$ and $Y_2$ represent H or lower alkyl having up to 4 carbon atoms such as methyl, ethyl, and isopropyl The compounds having formula IV are preferably those wherein Z represents hydrogen or lower alkyl having up to 4 carbon atoms such as methyl, ethyl, propyl or isopropyl.

The most preferred compound having formula I is arecoline wherein $R_1$ represents methoxy and $R_2$ represents methyl. The most preferred compound having formula II is physostigmine wherein $X_1$, $X_2$ and $X_3$ represent methyl and $X_4$ represents H. The most preferred compound having formula III is naloxone wherein $Y_1$ and $Y_2$ represent hydroxy. The most preferred compound having formula IV is nicotine wherein Z represents methyl.

The present invention further includes pharmaceutically acceptable carboxylate salts of compounds containing a carboxyl group and pharmaceutically acceptable acid addition salts of compounds containing amino groups. Some suitable carboxylate salts include, for example, the sodium, potassium, and ammonium salts. Some suitable acid addition salts of compounds containing an amino group include the hydrochloride, hydrobromide, salicylate, and tartrate salts.

An especially preferred embodiment of the present invention is a device containing, and a method utilizing, a mixture of compounds having formula I in combination with a compound having formula II. Preferably, the compound having formula I is arecoline and the compound having formula II is physostigmine. The weight ratio of the compound having compound formula I to the compound having formula II is 2–40:1, preferably 4–30:1, and most preferably 6–20:1.

The compounds of the present invention may be obtained commerically or may be synthesized by methods known in the prior art. Commercially, arecoline may be obtained from Inland Akaloid Company, St. Louis, Miss. Physostigmine may be obtained from O'-Neil, Jones and Feldman Pharmaceuticals. Naloxone may be obtained from Endo Laboratories, Inc.

The compounds of formula I including arecoline may also be obtained by the partial hydrogenation of nicotinic acid. The hydroxy group may optionally be converted into lower alkyl or amino optionally substituted by lower alkyl.

The compounds having formula II other than physostigmine may be prepared from physostigmine or by the same general methods used to prepare physostigmine.

The compounds having formula III other than naloxone wherein $Y_1$ and $Y_2$ represent hydroxy may be prepared from naloxone by converting the hydroxy groups into the corresponding lower alkoxy groups.

The compounds having formula IV other than nicotine wherein Z represents methyl may be prepared from nicotine or by the same general methods used to prepare nicotine.

The present invention is directed more specifically to a device containing a means whereby a compound as described above is administered at a continuous, controlled rate. Such devices are already known in the prior art. The administration of pharmaceutically active compounds from such devices may be transdermal or oral.

Some suitable transdermale devices are discribed in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The device suitable in the present invention may also deliver pharmaceutically effective compounds orally. In one such device, the pharmaceutically effective compound is encapsulated in a semi water-insoluble semipermeable membrane such as cellulose acetate A tiny orifice is provided in the encapsulating agent by means of a drill or a laser. When placed in the body of the patient or animal being treated, water is absorbed through the encapsulating material. The pharmaceutically effective compound is forced through the orifice by osmotic pressure in the desired, gradual, constant, and controlled manner Such systems are described in U.S. Pat. Nos. 3,760,805, 3,760,806, 3,764,984, 3,845,770, 3,916,899, and 3,987,790. In these systems, the pharmaceutically active compound may be in solid form or absorbed on ion exchange resins as in the so called Pennkinetic system.

Another system for oral administration in accordance with the present invention is described by Sheth and Leeson in U.S. Pat. No. 4,137,300. This patent describes a device containing a wax matrix.

The active compounds of the present invention are administered from a suitable device in any convenient and appropriate form. Liquid active agents may be administered in their pure form or in solution. Solid active compounds may be administered in solution or in suspension. The solvent or suspension medium may be aqueous or organic in nature. Suitable solvents or suspension media for compounds having formula I are water, ethanol, silicone fluid, and mineral oil.

In order to facilitate the administration of a compound from a device as described above, a flux enhancer may be added to the system. In a device for transdermal administration, the flux enhancer increases the rate across the skin. An example of a flux enhancer for a transdermal device is "azone"; see U.S. Pat. No. 3,989,816. Azone has the following formula:

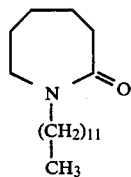

Azone may be placed on the skin in contact with the device, or may be contained in a resevoir optionally in the presence of a co-solvent. Other flux enhancers for transdermal devices include alcohols such as ethanol, DMSO, decyl methyl sulfoxide, and N-methyl lauramide.

Oral devices contain flux enhancers in order to increase the rate of release of the pharmaceutically effective compound from the device. Some suitable flux enhancers for oral devices include, for example, polyethylene glycol, hydroxypropyl methyl cellulose, and sugar.

Other materials may be added to the device along with the active compound. In a transdermal system, the rate of absorption through the skin may be dependent on pH. If so, a buffer may be introduced into the device in order to provide the optimum pH.

It is also desirable to introduce an anticholinergic agent which does not cross the blood brain barrier along with the active compound in order to block peripheral cholinergic side effects. Some suitable examples of anticholinergic agents include methscopolamine bromide; Sitaram et al, Science, 201, 274 (1978), and homatropine methyl bromide.

The present invention is further directed toward a method for treating memory impairment such as SDAT. The method comprises the oral or transdermal administration at a gradual, constant, and controlled rate of a compound in accordance with the present invention to a warm-blooded animal, such as a human being or other mammal. The dose is that effective to treat memory impairment, i.e. SDAT. For example, arecoline and its derivatives are administered at a rate of 0.1 to 10 mg/hr, preferably 0.5 to 5 mg/hr. Physostigmine and its derivatives are administered at a rate of 0.05 to 3 mg/hr, preferably 0.1 to 1 mg/hr. Naloxone and its derivatives are administered at a rate of 0.01 to 5 mg/hr, preferably 0.02 to 2 mg/hr. Nicotine and its derivatives are administered at a rate of 0.05 to 2.5 mg/hr preferably 0.02 to 2 mg/hr.

The preferred devices and methods of tha present invention are devices and methods for the transdermal administration of arecoline.

The partion coefficient (K) of a compound between an aqueous phase and mineral oil has been used as an indication of its potential to diffuse across skin. Permeability appears to be optimal when the partition coefficient is 1. Arecoline in pH 10 buffer (99.9% dissociation to the free base) yielded partition coefficients of 0.756 and 0.654 for concentrations of 1.0M and 0.01 M, respectively. Thus, arecoline in its free base form is expected to have good in vitro transdermal flux.

In order further to test the permeability of arecoline to human skin, the transdermal diffusion of aqueous arecoline was monitored using human cadaver skin mounted in, a Franz diffusion cell; see Current Problems in Dermatology, 7, 58 (1978) and the description of Franz diffusion cells and apparatus published by the Crown Glass Company, a copy of which may be found in the file history of this case. The flux, J, of each solution was calculated from a plot of change in concentration versus time.

The transdermal diffusion of arecoline was studied in several aqueous buffers from pH values of 6.4 to 9.0. This data is shown in Table 1. It is apparent that the rate of arecoline diffusion increases with increasing pH values.

Most of the skin samples were obtained from the back area of human cadavers. There was no systematic study to determine if the choice of donor-side would change the rate; however, it is presumed that the rate will be fastest in portions of the anatomy where the stratum corneum is relatively thin (chest, back, anterior forearm) and slowest where the stratum corneum is thickest (heel of hand, bottom of foot). There does not appear to be any difference in rate between Caucasian and Negro skin at pH values of 8 and 9. However, differences were observed between these two skin types in experiments at lower pH values.

The free base of arecoline appears to be the species that transfers across the stratum corneum. This allows some control of the transdermal flux by adjusting the pH value of the arecoline-containing solution. At a pH value of 9.0, approximately 85 mgs can be transferred across 5 cm$^2$ in 24 hours. This amount is in the upper range of useful doses for administration of arecoline. Lower doses can be administered by reducing the surface area and/or pH value. The formulator will therefore have a great deal of flexibility in designing a system that has the desired delivery characteristics.

A problem encountered with arecoline is its instability in solution. In alkaline buffers, the free base rapidly hydrolizes. Oxidation may also be a route of degradation. This difficulty may be controlled by limiting the pH value of the solution or by using an appropriate non-hydroxilic vehicle.

The rate and extent of arecoline delivery across human skin can be controlled by several factors. If zero order transfer is desired, it can be achieved by maintaining an excess of arecoline in the delivery vehicle. As long as this concentration remains constant, the rate will be a zero order function which can be limited in a transdermal device, for example, by a suitable membrane. The rate can be increased by increasing the surface area of the delivery system, increasing the concentration in the vehicle, or increasing the free base concentration by elevating the pH value.

Having generally described the invention, a more complete understanding can be obtained by reference to certain specific examples, which are provided herein for purposes of illustration only and are not intended to limit the claims unless otherwise specified

TABLE 1

TRANSDERMAL DIFFUSION OF ARECOLINE

| pH of 1 M Solution | Type of Skin # | Race of Skin Donor | Flux (mg/cm$^2$/hr.) | Mean Flux |
|---|---|---|---|---|
| 6.4 | RC | N | 0.017 | 0.017 |
| 7.0 | RB | C | 0.0545 | |
| | | | 0.0678 | 0.069* |
| | | | 0.0833 | |
| | RB | N | 0.0101 | |
| | | | 0.0057 | |
| 7.5 | RB | C | 0.1651 | |
| | | | 0.1486 | 0.185* |
| | | | 0.2246 | |
| | | | 0.2003 | |
| | RB | N | 0.0383 | |
| 8.0 | LB | C | 0.4524 | |
| | | | 0.3817 | 0.448 |
| | LB | N | 0.5000 | |
| | | | 0.4568 | |
| 9.0 | RB | C | 0.8551 | |
| | LB | C | 0.8868 | |
| | | | 0.8154 | 0.837 |
| | LB | N | 0.7419 | |
| | | | 0.8879 | |

RC — Right Chest
RB — Right Back
LB — Left Back
+ N = Negro
C = Caucasian
*Mean Flux does not include the Negro skin at these pH's as in these experiments diffusion through Negro skin was found to be significantly lower than that of Caucasian skin.

EXAMPLES

1. Preparation of Arecoline Free Base

Ten grams of arecoline HBr was dissolved in a minimal quantity (approximately 25 ml) of water and adjusted to pH 10 with saturated KOH in a separatory funnel. One hundred mls of petroleum ether was added and the layers were mixed. NaCl was then added to saturate the aqueous layer. The organic layer was collected, and the aqueous layer was extracted three more times with petroleum ether. The combined organic layers were transferred to a 500 ml round bottom flask, boiling chips were added and the petroleum ether was removed by distillation. The remaining oil was layered with $N_2$ and stored in low-actinic glassware. The oil was anlyzed by NMR to show the absence of a halogen component.

2. Transdermal Diffusion of Arecoline Through Human Skin

Franz diffusion cells utilize the finite dose technique of in vitro drug delivery. Human cadaver skin was mounted in a diffusion chamber where it remined in constant contact with solution on both sides. The stratum corneum was in contact with a thin layer of concentrated drug in solution (donor side). The receiver side contained a constantly stirred, isotonic saline solution maintained at 32° C. Diffusion of the compound was monitored by removing aliquots from the receiver side and analyzing these samples by HPLC.

The human skin used in all experiments was obtained from a medical school. All cadavers were refrigerated at death and excision was performed within 24 hours post-mortem. The skin was first treated witb Betadine surgical scrub (Povidone-Iodine solution) and surfactant (the skin was scrubbed if dirty), rinsed with sterile water and then with Betadine rinse solution. The skin was then air-dried and swabbed with mineral oil prior to excision. A dermatome was used for excising the skin to −0.0015 in. (−350 microns) thickness. Saline solution was used to rinse the excess mineral oil from the skin prior to treatment with Eagle's minimole essential medium (minerals, amino acids and sugars). To this solution, 15% glycerol was added and the skin was allowed to set for two hours. It was then removed from solution, packaged and frozen in liquid $N_2$. The samples, packed in dry ice were shipped in styrofoam containers and kept frozen until use.

For the flux experiments, skin samples were removed from the freezer and thawed immediately prior to use. The samples were examined visually for any tears or holes, then cut into smaller pieces, peeled from the gauze backing and mounted across the diffusion chamber with the stratum corneum side up. The donor-side cap was placed on top and the unit was clamped in place. The receiver-side was filled with a saline solution and stirred. The material in the receiver-side was sterile normal saline solution, which was adjusted to approximate the tonicity of the buffer solution on the donor-side. One ml of the drug solution was pipeted onto the donor-side of the skin and 50 microliter aliguots were withdrawn from the receiver-side at the various time intervals. These samples were injected onto an HPLC column under the aforementioned conditions.

The donor solutions were prepared as 1.0M (approximately 20% W/V) arecoline HCl or arecoline HBr in a phosphate, citrate, borate buffer adjusted to various pH values. Each flux experiment was repeated three to five times.

Having now fully described the invention, it will be apparent to one of ordinary skill in the art that many changes and modifications can be made thereto without departing from the spirit or scope of the invention as set forth herein.

What I claim is:

1. A device for the transdermal administration of a drug for the treatment of memory impairment comprising
   (a) a drug impermeable backing layer;
   (b) a drug permeable rate controlling membrane sealed to one side of said backing layer as to define at least one drug reservoir compartment therebetween;
   (c) an adhesive layer;
   (d) a drug or composition thereof within said hollow drug reservoir;
   said drug comprising a memory improving effective amount of a compound having the formula

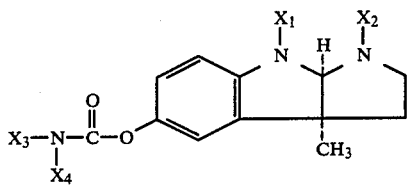

wherein $X_1$, $X_2$, $X_3$, $X_4$, independently represent H or lower alkyl; said composition comprising said drug and at least one pharmaceutically acceptable adjunct; whereby said drug is delivered in a controlled, continuous manner to a patient to which said device has been applied.

2. A method of treating memory impairment in a mammal in need thereof comprising administering to said patient the device of claim 1 so that a continuous memory impairment treating effective amount of said drug is delivered to said mammal in a controlled manner.

3. The method of claim 2 wherein said memory impairmemt is senile dementia of the Alzheimer's type.

4. The device of claim 1 wherein the compound is physostigmine.

5. The device of claim 1 wherein the compound is combined with a suitable excipient.

6. The device of claim 1 further comprising an anticholinergic agent in an amount to reduce cholinergic side effects wherein the anticholinergic agent does not cross the blood brain barrier.

7. The device of claim 6 wherein the anticholinergic agent is methscopolamine.

8. The device of claim 6 wherein the anticholinergic agent is homatropine methyl bromide.

9. The method of claim 2 wherein the compound is physostigmine.

10. The method of claim 2 wherein the compound is combined with a suitable excipient.

11. The method of claim 2 further comprising administering an anticholinergent agent in an amount to reduce cholinergic side effects wherein the anticholinergent agent does not cross the blood brain barrier.

* * * * *